(12) United States Patent (10) Patent No.: US 12,636,079 B2

Batchelor (45) Date of Patent: May 26, 2026

(54) TRIPOLAR ELECTROSURGICAL ELECTRODE AND CONTROL

(71) Applicant: GYRUS ACMI, INC., Westborough, MA (US)

(72) Inventor: Kester Julian Batchelor, Mound, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 936 days.

(21) Appl. No.: 17/653,351

(22) Filed: Mar. 3, 2022

(65) Prior Publication Data

US 2022/0280231 A1 Sep. 8, 2022

Related U.S. Application Data

(60) Provisional application No. 63/157,270, filed on Mar. 5, 2021.

(51) Int. Cl.
*A61B 18/16* (2006.01)
*A61B 18/00* (2006.01)

(52) U.S. Cl.
CPC .... *A61B 18/16* (2013.01); *A61B 2018/00577* (2013.01); *A61B 2018/00595* (2013.01); *A61B 2018/00625* (2013.01); *A61B 2018/00702* (2013.01); *A61B 2018/00875* (2013.01)

(58) Field of Classification Search
CPC .......... A61B 18/16; A61B 2018/00577; A61B 2018/00595; A61B 2018/00625; A61B 2018/00875
See application file for complete search history.

(56) References Cited

U.S. PATENT DOCUMENTS

| | | | | |
|---|---|---|---|---|
| 6,565,560 B1* | 5/2003 | Goble | ................. | A61B 18/149 |
| | | | | 606/171 |
| 6,896,674 B1* | 5/2005 | Woloszko | ............ | A61B 18/148 |
| | | | | 604/35 |
| 2003/0120269 A1* | 6/2003 | Bessette | ................ | A61B 18/14 |
| | | | | 606/32 |
| 2008/0188840 A1* | 8/2008 | Johnson | ............... | A61B 18/203 |
| | | | | 606/9 |
| 2011/0196364 A1* | 8/2011 | Morris | ............... | A61B 18/1402 |
| | | | | 606/41 |
| 2018/0344382 A1* | 12/2018 | Brockmann | ........... | A61B 18/14 |
| 2019/0133673 A1* | 5/2019 | Boll | ....................... | A61B 18/14 |
| 2020/0397500 A1* | 12/2020 | Woloszko | .......... | A61B 18/1482 |
| 2021/0298811 A1* | 9/2021 | Dijkstra | ................ | A61B 18/16 |

* cited by examiner

*Primary Examiner* — Joseph A Stoklosa
*Assistant Examiner* — Annie L Shoulders
(74) *Attorney, Agent, or Firm* — Schwegman Lundberg & Woessner, P.A.

(57) ABSTRACT

Electrosurgical devices that reduce surgery time while still adhering to surgical standards are provided. An electrosurgical device can include a tripolar configuration. A primary electrode can be used to generate a vapor pocket. A secondary electrode can be activated after the vapor pocket is generated. The vapor pocket can be steered to be between the primary and secondary electrodes and a surgery target.

24 Claims, 7 Drawing Sheets

802 PROVIDE ENERGY TO A FIRST ELECTRODE OF AN ELECTROSURGICAL DEVICE

804 DETECT THAT A VAPOR POCKET IS GENERATED BY THE FIRST ELECTRODE

806 IN RESPONSE TO DETECTING THAT THE VAPOR POCKET IS GENERATED, ELECTRICALLY CONNECT A SECOND ELECTRODE TO THE ENERGY SUPPLY WHILE THE FIRST ELECTRODE REMAINS CONNECTED TO THE ENERGY SUPPLY

TRIPOLAR ELECTROSURGICAL ELECTRODE AND CONTROL

RELATED APPLICATION

This application claims the benefit of priority to U.S. Provision Patent Application No. 63/157,270, titled "Tripolar Electrosurgical Electrode and Control", and filed on Mar. 5, 2021, which is incorporated herein by reference in its entirety.

FIELD

These teachings regard electrode configurations for improving vapor pocket retention and control, such as for tissue vaporization.

BACKGROUND

Some electrosurgical devices vaporize tissue by creating a gas pocket in a fluid. The gas pocket can, in general, be created between an active and return electrode. The active electrode can be part of the electrosurgical device. The return electrode can be part of the electrosurgical device or can include a pad situated as a ground pad on a patient.

More particularly, some electrosurgical devices can activate in a saline or glycine environment. These electrosurgical devices can apply energy (e.g., ultrasonic or electrical energy), which causes the fluid around the active electrode to boil. The boiling causes a vapor pocket to form. That vapor pocket is a medium through which tissue can be vaporized. In general, any tissue that comes into contact with the vapor pocket is vaporized. As electrodes get larger, the vapor pocket is larger, and more tissue can be vaporized at once, but more energy is consumed.

SUMMARY

The present teachings provide electrosurgical systems, devices, methods, and computer-readable media that can control a location or retention of a generated vapor pocket. The present teachings can provide a device including at least two electrodes, and a suction port situated to draw a vapor pocket generated by a first electrode towards another electrode.

The teachings can provide vapor pocket retention using a tripolar electrode, or an electrosurgical device with two or more active electrodes and one or more return electrodes. The tripolar electrode can include multiple electrodes that perform vaporization, sometimes called active electrodes, and one or more return electrodes. The active electrodes are not always actively energized but are rather selectively energized. Selectively energizing the electrodes can keep the energy consumption relatively low, while effectively increasing a size of a vapor pocket through which energy travels from the device to the tissue target.

An electrosurgical device can include a return electrode through which energy travels back to a power source (e.g., ground). The electrosurgical device can include first and second electrodes. The first electrode can be energized to establish a vapor pocket. Energy supplied to the first electrode can be reduced to a level that retains the vapor pocket and sufficient for tissue vaporization after the vapor pocket is established.

The second electrode can be energized to a level sufficient for tissue vaporization. The first and second electrodes can concurrently vaporize tissue. This concurrent vaporization can increase a tissue vaporization rate (an amount of tissue vaporized per unit time) of the electrosurgical device. This increased vaporization rate can reduce an amount of time to perform a surgery.

The electrosurgical device can include a suction port. The second electrode can be situated proximate the suction port. The suction port can be situated such that it draws the established vapor pocket towards the second electrode. Energy from the second electrode can help retain the vapor pocket, vaporize tissue, or a combination thereof. The second electrode can surround the suction port. The second electrode can circumscribe the suction port.

The first electrode, second electrode, or both can include a dielectric covering a portion of a surface facing the tissue. The dielectric covering can help control a location at which energy exits the electrode(s) to vaporize tissue. These points are sometimes called Nidus points.

The electrosurgical device can include a fluid outlet port. The fluid outlet port can be situated to direct the vapor pocket towards the second electrode. The fluid outlet port can be situated on a first side of the first electrode. The second electrode can be situated on a second side of the first electrode. The first side can be opposite the second side.

The electrosurgical device can include a switch component configured to connect both the first electrode and the second electrode to an energy supply. The switch can be an electronically controllable switch.

An electrosurgical system can include the electrosurgical device and an energy supply coupled to the electrosurgical device. The energy supply can be configured to provide energy to the electrosurgical device. The energy supply can include control circuitry configured to, in response to detecting a vapor pocket at the first active electrode, electrically connecting the second electrode to the energy concurrently with the first electrode.

Detecting the vapor pocket can include determining a resistance to power of the energy supply has increased by a first criterion. Detecting the vapor pocket can include determining a phase angle of power from the energy supply has changed by a second criterion. Detecting the vapor pocket can include determining a current of power from the energy supply has decreased by a third criterion. Detecting the vapor pocket is generated can include determining a voltage of power from the energy supply has increased by a fourth criterion.

The control circuitry can be configured to reduce a magnitude of the power provided to the first electrode, second electrode, or both in response to detecting the vapor pocket. The control circuitry can be configured to activate the suction port in response to detecting the vapor pocket. The control circuitry is configured to deactivate the suction port in response to detecting that the vapor pocket has at least partially dissipated.

The control circuitry can be configured to cause fluid to flow to the fluid outlet port in response to detecting the vapor pocket. The control circuitry can be configured to restrict fluid flow in the fluid outlet port in response to detecting that the vapor pocket has dissipated.

DETAILED DESCRIPTION

Figure 1:
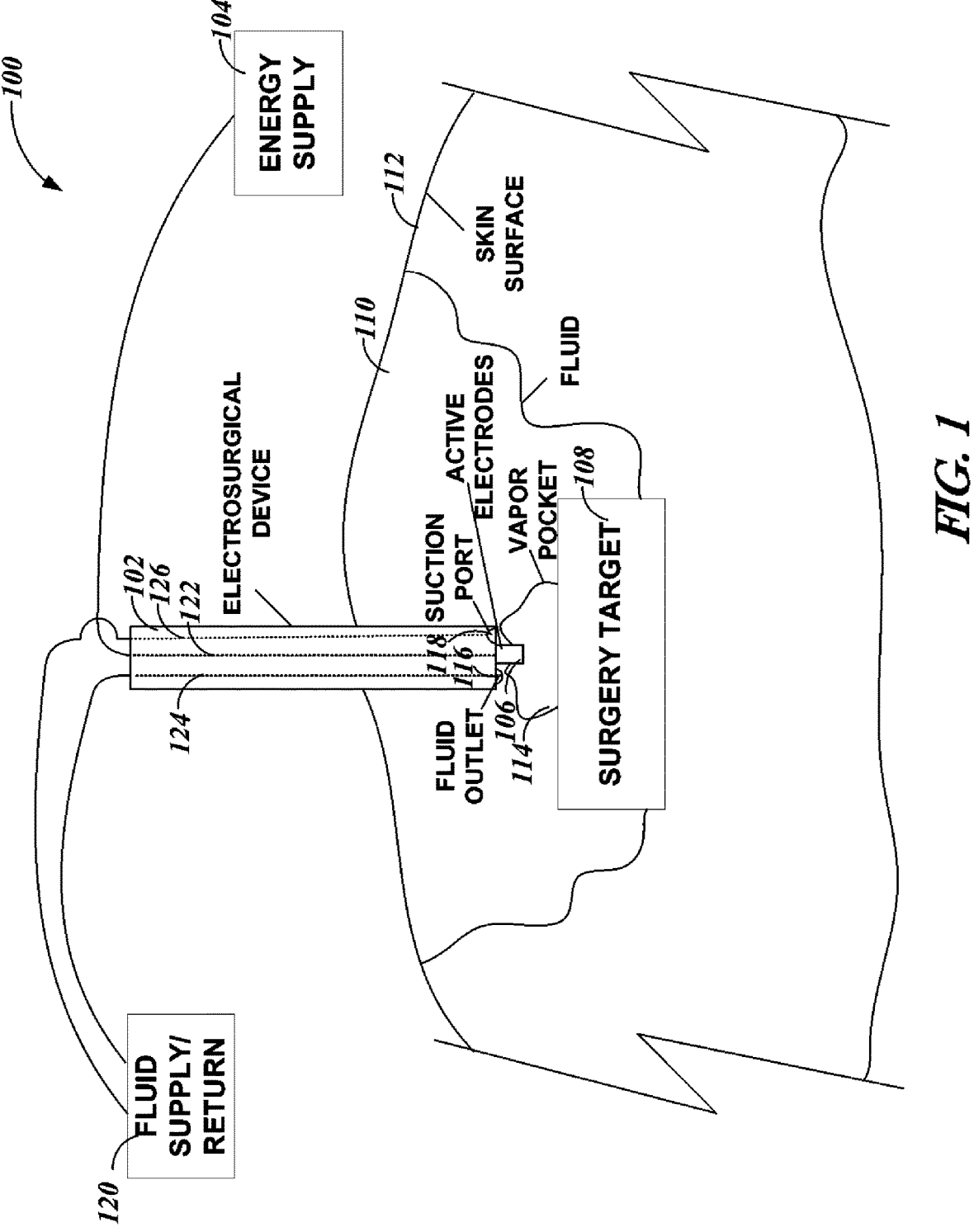
FIG. 1 illustrates, by way of example, a diagram of an embodiment of a system for surgically altering tissue.

A fluid, such as physiologic saline or glycine, can be introduced into a patient cavity, such as to distend the cavity. The distension of the cavity can increase an amount of space in the cavity, thus providing more room to perform surgery. An electrosurgical device can be situated in the fluid that was introduced into the patient cavity. The electrosurgical device can surgically alter tissue in the cavity through a vapor pocket. To alter (e.g., cauterize, ablate, remove, vaporize, or the like) the tissue, the electrosurgical device can form a vapor pocket in the fluid. The electrosurgical device can retain the vapor pocket while consuming less power than is used in generating the vapor pocket. However, the vapor pocket can dissipate or become dislodged and the space consumed by the vapor pocket can be consumed by the fluid. Then, to alter further tissue, the vapor pocket can be re-established.

The power (e.g., electrical current, electrical voltage, or a combination thereof) consumed in establishing the vapor pocket can be prohibitively high. Surgical standards dictate that a limited amount of wattage can be applied to a patient at a given point in time and on average. The limit is currently about 300 Watts, about 400 Watts, or the like. This power limit restrains the size of the electrode. A smaller electrode can establish the vapor pocket with lower energy than a larger electrode. The vapor pocket generated by the smaller electrode is smaller than the vapor pocket generated by the larger electrode. The power and size of the vapor pocket limits control the amount of tissue that can be altered per unit time.

In generating the vapor pocket, a larger electrode consumes more energy than a smaller electrode. The energy consumed can be above the surgical standards. This forces use of a smaller electrode in establishing the vapor pocket. The smaller electrode cannot vaporize as much tissue as a larger electrode.

Teachings can use a first electrode to establish the vapor pocket. The first electrode can be configured such that power consumed in generating the vapor pocket does not violate surgery standards. Teachings can then reduce energy provided to the first electrode. The reduction in energy can be to a level sufficient to maintain the vapor pocket and less than the energy used to generate the vapor pocket. Teachings can provide energy to a second electrode, thus increasing an area that vaporizes tissue. This increase in area, effectively increases the size of the active electrode while still maintaining operation of the electrosurgical device within surgical standard limits.

The electrosurgical device, or a device coupled thereto, can detect when the vapor pocket is formed. The detection can include identifying that a resistance, phase, current, voltage, or other parameter of energy consumed by the electrosurgical device has satisfied one or more criterion. The electrosurgical device can include a fluid outlet port or a suction port. The fluid outlet port or the suction port can be situated such that, when in operation, the vapor pocket is deflected towards the second electrode.

FIG. 1 illustrates, by way of example, a diagram of an embodiment of a system 100 for surgically altering tissue. The system 100 as illustrated includes an electrosurgical device 102, an energy supply 104, and a fluid supply/return 120. The electrosurgical device 102 can include or use an endoscope, laparoscope, arthroscope, or a dedicated cautery or ablation tool, or a minimally-invasive device or the like. The electrosurgical device 102 can include a monopolar or bipolar electrode 106 for cautery, ablation, vaporization, or the like, of a surgery target 108. A region around the surgery target 108 can be at least partially filled with a conductive fluid 110, such as physiologic saline or glycine. The surgery target 108 can be internal to a patient and can be accessed through a natural or manmade orifice, such as a hole through skin 112 of the patient.

The electrosurgical device 102 can be used for dissection, resection, vaporization, desiccation, coagulation, or a combination thereof. Example urologic surgeries that can be performed using the electrosurgical device include urethroscopy, cystoscopy, ureteroscopy, nephoscopy, and percutaneous surgery. Urological procedures may include electrovaporization of the prostate gland (EVAP), transurethral resection of the prostate (TURP), interstitial ablation of the prostate gland by a percutaneous or periurethral route, transurethral or percutaneous resection of urinary tract tumors, division of strictures, ureter, ureteral orifice, bladder neck or urethra, correction of ureterocele, shrinkage of bladder diverticular, cystoplasty procedures, thermally induced shrinkage of the pelvic floor, excision of diseased tissue, hemostasis, or a combination thereof. Examples of arthroscopic surgeries include meniscectomy of the knee joint, lateral retinacular release of the knee joint, removal of anterior or posterior cruciate ligaments or remnants thereof, labral tear resection, acromioplasty, bursectomy and subacromial decompression of the shoulder joint, anterior release of the temporomandibular joint, synovectomy, cartilage debridement, chondroplasty, division of intra-articular adhesions, fracture and tendon debridement, inducing thermal shrinkage of joint capsules, subluxation to any articulated joint of the body, discectomy of a disc prolapse or as part of a spinal fusion, excision of diseased tissue, hemostasis, or a combination thereof.

The electrosurgical device 102, in an active state, can vaporize a portion of the fluid 110. The vaporization of the fluid 110 can form a vapor pocket 114 in the fluid 110. When the vapor pocket 114 extends between the electrode 106 and the surgery target 108, focused energy can flow from the electrode 106 to the surgery target 108. The electricity incident on the surgery target 108 can ablate, cauterize, or otherwise alter the surgery target 108. The result can be removal, hardening, or closure of the surgery target 108, for example.

More power is used to generate the vapor pocket 114 than is required to alter the surgery target 108 and concurrently maintain the vapor pocket 114. A spike of electricity from the energy supply 104 can help generate the vapor pocket 114. Then the energy from the energy supply 104 can be reduced to a level that maintains the vapor pocket 114 and alters the surgery target 108. This reduction in energy can allow the electrode 106 to be made larger or the surgery to last longer without violating the surgical standards.

At some point, however, the vapor pocket 114 can collapse or otherwise dissipate. The vapor pocket 114 dissipation can be due to the energy from the energy supply 104 being reduced below a threshold required to maintain the vapor pocket 114, the active electrodes 106 moving too far away from the surgery target 108, fluid intrusion into the vapor pocket 114, among others. To continue altering the surgery target 108, the electrical power from the energy supply 104 can be increased to re-establish the vapor pocket 114.

The active electrodes 106 can include multiple electrodes coupled to the energy supply 104 through one or more electrical paths 122. The active electrodes 106 can include a first electrode configured to establish the vapor pocket 114 while keeping energy consumption below surgical standards. The active electrodes 106 can include a second electrode configured to be switched to an active state after the vapor pocket 114 is established. The second electrode can effectively increase a size of the vaporizing surface area of the electrosurgical device.

The electrosurgical device 102 as illustrated includes a fluid outlet port 116. The fluid outlet port 116 can include a lumen 124 coupled to the fluid supply/return 120. The fluid supply/return 120 can include one or more pumps to provide the fluid 110 to or remove the fluid 110 from a cavity. The fluid outlet port 116 can provide fluid 110 from the fluid supply/return 120 to the cavity in which the electrosurgical device 102 is inserted via the lumen 124. The fluid 110 can help in distension of the cavity, cooling of the surgery target 108, cooling of a region proximate the surgery target 108, or a combination thereof. The fluid 110 from the fluid outlet port 116 can deflect the vapor pocket 114 towards the second electrode of the active electrodes 106 (shown in more detail elsewhere).

The electrosurgical device 102 as illustrated includes a suction port 118. The suction port 118 can include a lumen 126 coupled to the fluid supply/return 120. The suction port 118 can remove fluid 110 from the cavity, via the lumen 126, in which the electrosurgical device 102 is inserted. The suction port 118 can cause circulation of the fluid 110, such as to help reducing distension of the cavity, cooling of the surgery target 108, cooling of a region proximate the surgery target 108, or a combination thereof. The suction port 118 can pull the vapor pocket 114 towards the second electrode of the active electrode 106 (shown in more detail elsewhere).

The action of the fluid outlet port 116 can help in retaining the vapor pocket 114 in a location at which both the first and second electrodes, or other electrodes of the electrodes 106, can transmit energy to the surgery target 108. The action of the suction port 118 can, similarly, help in retaining the vapor pocket 114 in a location at which both the first and second electrodes, or other electrodes of the electrodes 106, can transmit energy to the surgery target 108.

Figures 2, 3:
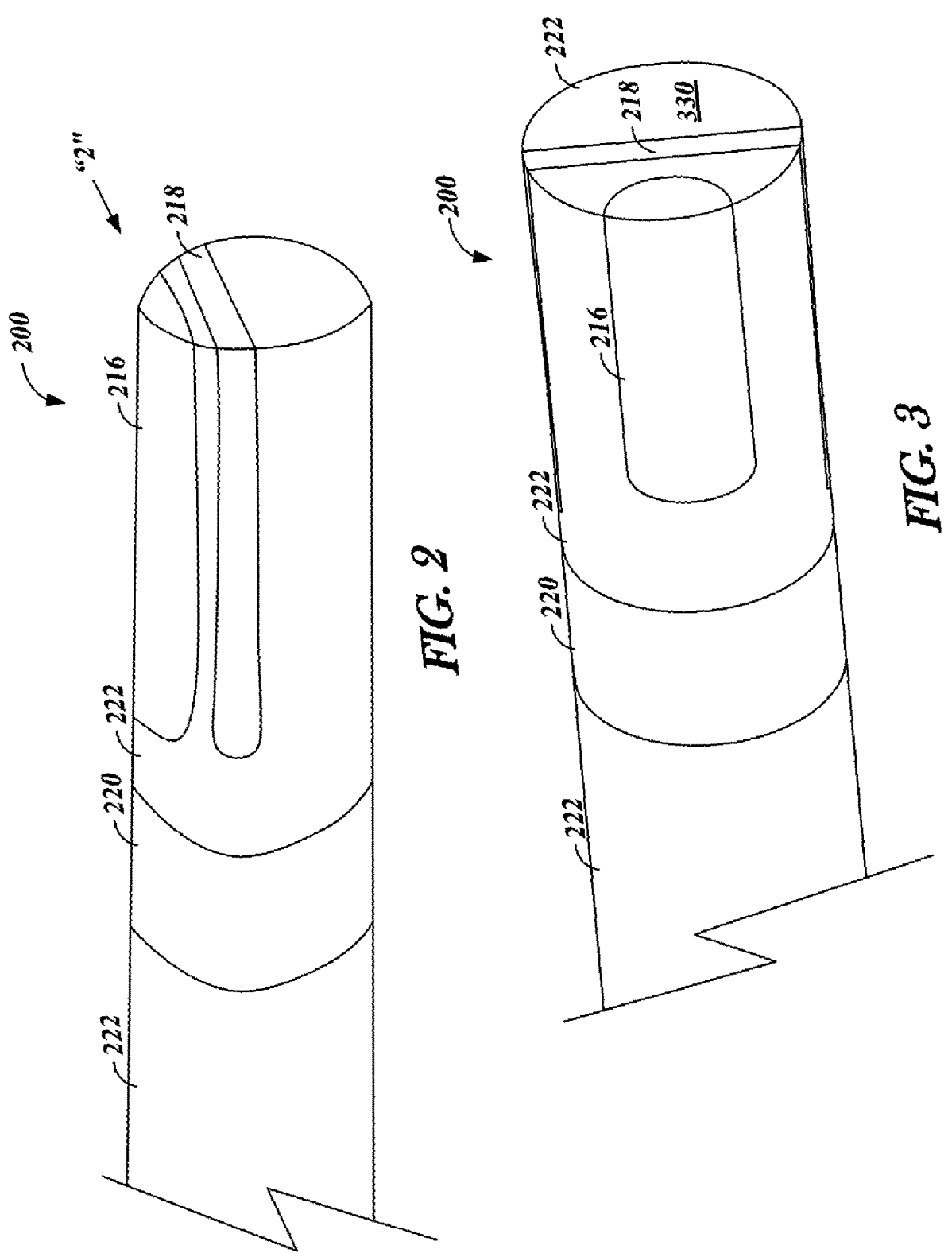
FIG. 2 illustrates, by way of example, a diagram of an electrosurgical device.
FIG. 3 illustrates, by way of example, a perspective view diagram of the electrosurgical device from a perspective indicated by an arrow labeled "2" in FIG. 2.

FIG. 2 illustrates, by way of example, a diagram of an electrosurgical device 200. The electrosurgical device 200 of FIG. 2 is a tripolar device but could include more than three electrodes. The electrosurgical device 200 includes electrodes 216, 218 and a return electrode 220. The active electrodes 216, 218 can include the surface from which energy from the energy supply 104 (see FIG. 1) exits the electrosurgical device 200 towards the surgery target 108 (see FIG. 1). The return electrode 220 completes the electrical path for electricity to travel back to the energy supply 104. The return electrode 220 can be electrically coupled to electrical ground.

The electrosurgical device 200 further includes a dielectric material 222. The dielectric material 222 can electrically isolate the active electrode 216, the active electrode 218 and the return electrode 220 from each other. The dielectric material 222 can include any electrically isolating material that can be safely used within the body, such as, for example, ceramic, or more particular representative embodiments including alumina oxide (Al2O3), Zirconia Toughened Alumina (ZTA), or the like.

In use, the active electrode 216 or 218 can be individually powered using the energy supply 104 (see FIG. 1). The active electrode 216 or 218 can generate energy sufficient to create the vapor pocket 114 (see FIG. 1). After the vapor pocket 114 is generated, the other active electrode 218 or 216 can be powered. The active electrodes 216 and 218 can then concurrently alter the therapy target 108. Altering the therapy target 108 can include energy arcing from the electrodes 216 and 218 through the vapor pocket 114 and to the surgery target 108. After the vapor pocket is established, the energy provided by the energy supply 104 can be reduced to a level that retains the vapor pocket 114 and still allows energy arcs to travel from the electrodes 216 and 218 to the surgery target 108.

FIG. 3 illustrates, by way of example, a perspective view diagram of the electrosurgical device 200 from a perspective indicated by an arrow labeled "2" in FIG. 2. The electrodes 216, 218 extend to an end 330 of the electrosurgical device 200. In some instances, one or more of the electrodes 216, 218 do not extend to the end 330. In such instances, the one or more electrodes 216, 218 are exposed along an outer surface of the electrosurgical device 200 at a location other than the end 330.

Figure 4:
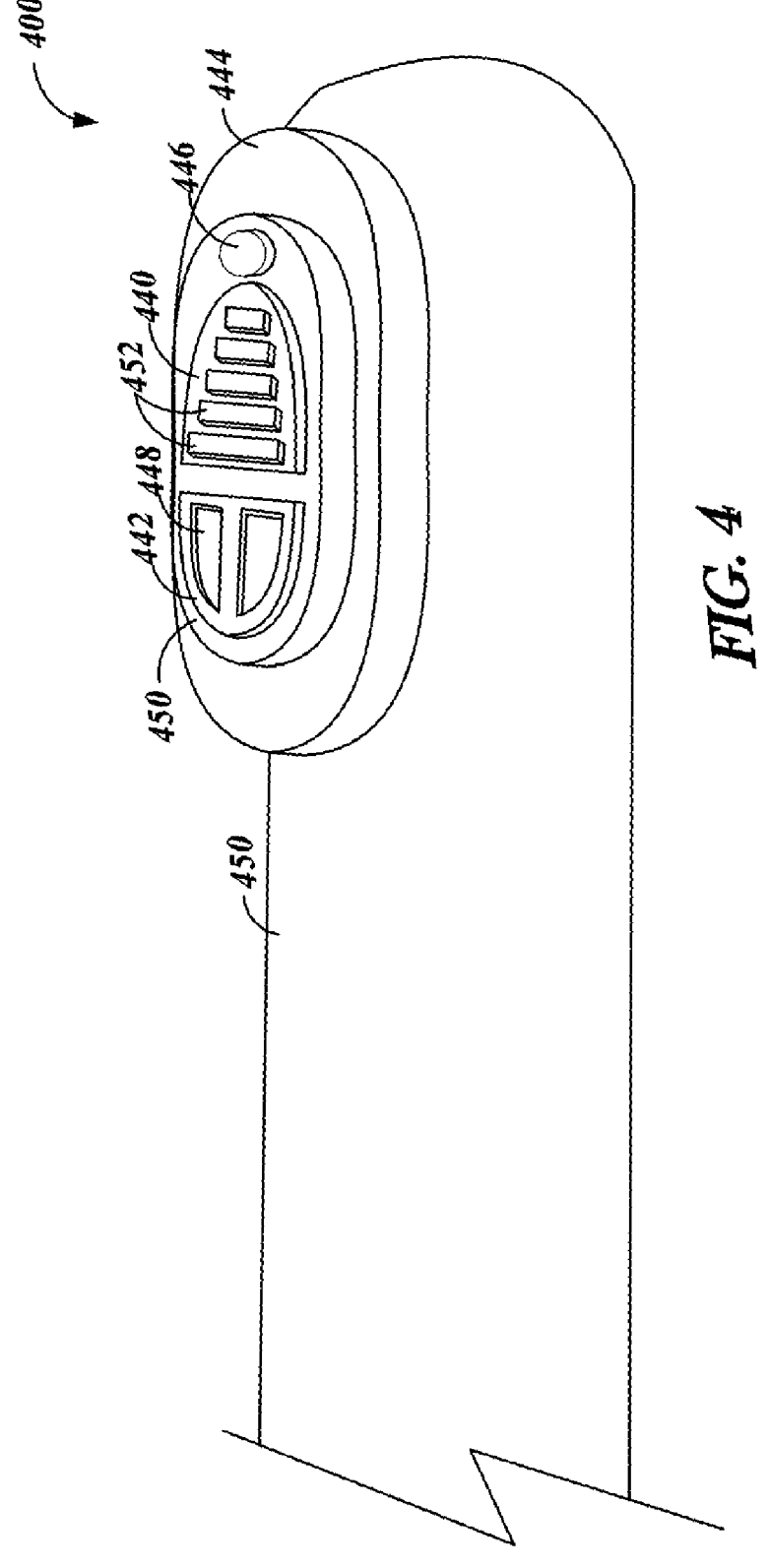
FIG. 4 illustrates, by way of example, a diagram of an embodiment of a tripolar electrode electrosurgical device.

FIG. 4 illustrates, by way of example, a diagram of an embodiment of a tripolar electrode electrosurgical device 400. The electrosurgical device 400 as illustrated includes electrodes 440, 442 situated to provide energy to the surgery target 108. The electrodes 440, 442 can perform functions similar to electrodes 216, 218, respectively, of the electrosurgical device 200. The electrode 440 can be considered a primary electrode. The primary electrode can be the electrode through which the vapor pocket 114 is established in the fluid 110. The electrode 442 can be considered a secondary electrode. The secondary electrode can be the electrode that is energized after the vapor pocket 114 is established. The electrodes 440, 442 are electrically separated by a dielectric material 450. The dielectric material 450

A return electrode 444 can be separated from the electrodes 440, 442 by a dielectric material 450. The return electrode 444 can perform a same function as the return electrode 220. The dielectric material 450 can perform a same function as the dielectric material 222.

The electrosurgical device 400 further include a fluid outlet port 446. The fluid outlet port 446 can receive fluid from the fluid supply/return 120 (see FIG. 1). The fluid outlet port 446 can be activated to provide fluid 110 to a cavity in which the surgery target 108 is situated. The fluid 110 provided by the outlet port 446 can include saline, glycine, or the like. The fluid outlet port 446 can be situated on a side of the electrode 440 that is opposite the electrode 442. In such a configuration, when fluid 110 is provided through the outlet port 446, the vapor pocket 114 can be deflected towards the electrode 442 (see FIGS. 6 and 7 and elsewhere for more details).

The electrosurgical device 400 further includes a suction port 448. The suction port 448 can be activated to remove fluid 110 from the cavity in which the surgery target 108 is situated. The suction port 448 can provide the fluid 110 to the fluid supply/return (see FIG. 1). The suction port 448 can be situated on a side of the electrode 440 that is opposite the fluid outlet port 446. The suction port 448, when activated, can draw in the fluid 110. In drawing in the fluid 110, the suction port 448 can draw the vapor pocket 114 towards the electrode 442.

The action of the activated fluid outlet port 446, suction port 448, or a combination thereof can help position the vapor pocket 114 between both the electrodes 440, 442 and the surgery target 108. With the vapor pocket 114 situated between both the electrodes 440, 442 and the surgery target 108, both of the electrodes 440, 442 can alter the surgery target 108 through the vapor pocket 114.

The electrode 440 can include another dielectric 452 situated thereon. The dielectric 452 can help control a location of a Nidus point of the electrode 440. The Nidus point is a location from which energy arcs from the electrode 440 to the surgery target 108 and also a point from which the vapor pocket 114 is most likely to develop.

The electrode 442 can be situated proximate the suction port 448. The electrode 442 can circumscribe or otherwise at least partially surround the suction port 448. In such a configuration, the suction port 448 can draw the vapor pocket 114 towards the electrode 442.

Figure 5:
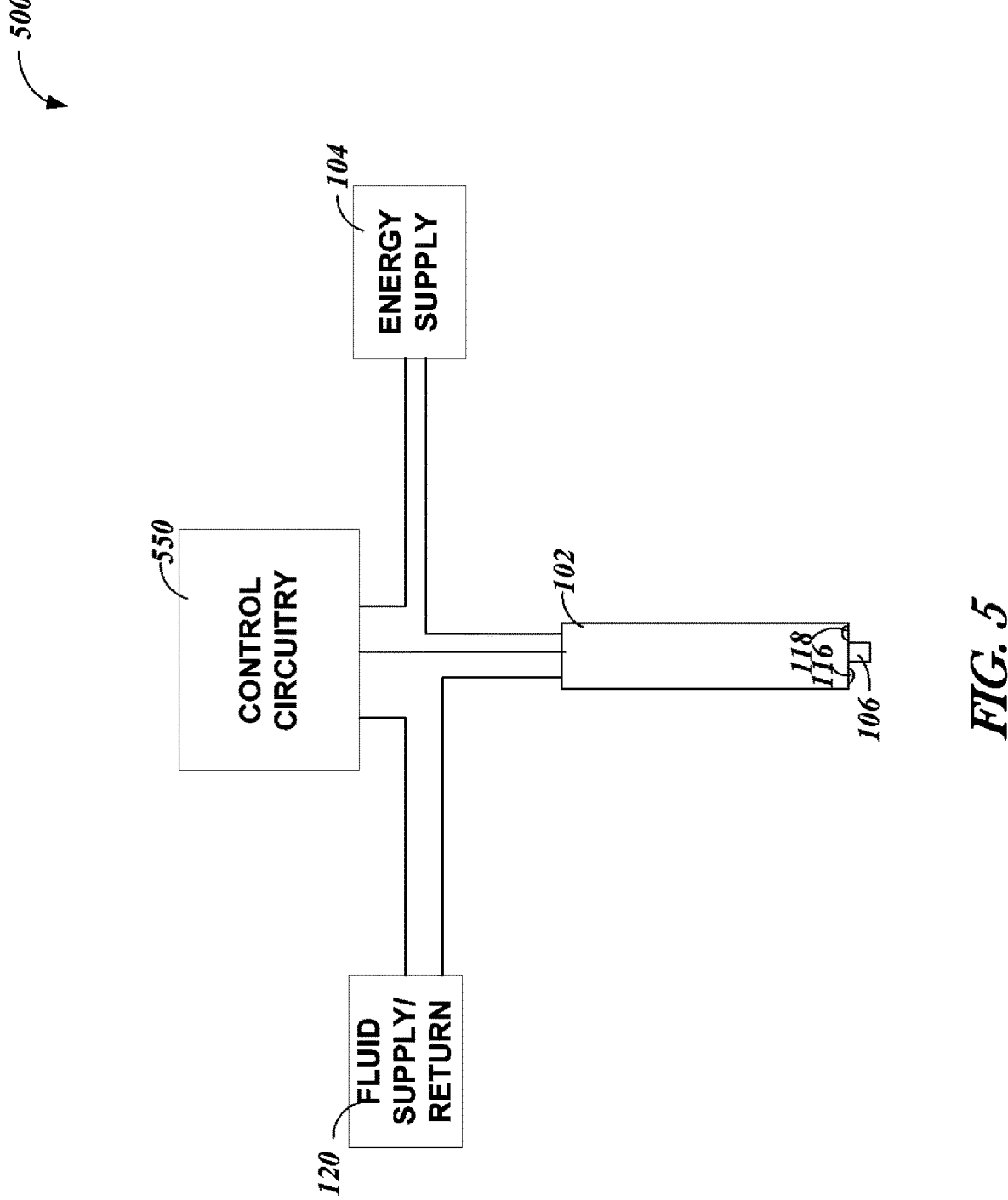
FIG. 5 illustrates, by way of example, a diagram of an embodiment of an electrosurgical system that includes the electrosurgical device of one of FIGS. 1-4.

FIG. 5 illustrates, by way of example, a diagram of an embodiment of an electrosurgical system 500 that includes the electrosurgical device 102. The electrosurgical device 102 can include three or more electrodes. The three or more electrodes can include multiple active electrodes (electrodes that actively perform the alteration of the surgery target 108) and one or more return electrodes. The electrosurgical device 400 can be used in place of the electrosurgical device 102.

The system 500 as illustrated includes control circuitry 550 communicatively coupled to the energy supply 104, the fluid supply/return 120, and the electrosurgical device 102. The control circuitry 550 can include electric or electronic components electrically connected to provide data or control whether energy is provided to the first electrode, second electrode, another electrode, or a combination thereof. The electric or electronic components can include one or more resistors, transistors, capacitors, diodes, inductors, processing units (e.g., central processing units (CPUs), application specific integrated circuits (ASICs), field programmable gate arrays (FPGAs), graphics processing units (GPUs), or the like), logic gates (e.g., AND, OR, XOR, negate, buffer, or the like), power supplies, oscillators, switches, amplifiers, analog to digital converters, digital to analog converters, transducers, or the like. The control circuitry 550 can be an independent component or part of the energy supply 104, the fluid/supply return 120, or the electrosurgical device 102.

The control circuitry 550 can be configured to detect when the vapor pocket 114 is present. Electrical characteristics of the energy drawn from the energy supply 104 can indicate whether the vapor pocket 114 is present. For example, the control circuitry 550 can include a transducer for measuring electrical conductivity, resistivity, impedance, phase angle, reactance, resistance, capacitance, and inductance, or one or more combinations thereof, of the surgery environment. In some cases, the electrical sensor can include one or more of the electrodes 106, such as in combination with one or more other electrode or internal or external transducer or transducer interface components.

In some examples, the control circuitry 550 can include one or more passive components, such as a resistor, capacitor, diode, a combination thereof, or the like. The control circuitry 550 can be situated in the electrosurgical device 102, 200, 400. The control circuitry 550 can be situated in an electrical path coupled between the first electrode and the second electrode. The control circuitry 550 can be configured to allow energy to flow to the second electrode when the resistance in the first electrode is greater than a threshold. In this manner, the control circuitry 550 can passively control whether energy is provided to the second electrode.

In one or more examples, the control circuitry 550 can include a timer. The control circuitry 550 can activate the timer about the time energy is provided to the first electrode. The control circuitry 550 can then can provide energy to the second electrode after a specified period of time has elapsed. For example, the electrical transducer can be used to detect the real-valued or complex-valued electrical impedance or electrical conductance experienced by energy from the electrodes 106 (e.g., electrical conductivity, electrical resistivity, electrical impedance, electrical conductance, phase angle, reactance, resistance, capacitance and inductance, or the like). A surgical environment that includes the vapor pocket 114 can be less electrically resistive than a surgical environment that includes the vapor pocket 114. Thus, detecting the vapor pocket includes determining a resistance to power of the energy supply has increased by a first criterion.

An electrode in a surgical environment with the vapor pocket 114 can draw energy of a first phase angle, while an electrode in a surgical environment without the vapor pocket 114 can draw energy of a second, different phase angle. Thus, detecting the vapor pocket 114 is present includes determining a phase angle of power from the energy supply 104 has changed by a second criterion (e.g., wherein the second criterion is indicative of the phase angle change between the first and second phase angles).

An electrode in a surgical environment without the vapor pocket 114 can draw energy of a first current, while an electrode in a surgical environment with the vapor pocket can draw energy of a second current. The first current is less than the second current. Thus, detecting the vapor pocket 114 is present can include determining the current of power from the energy supply 104 has changed by a third criterion (e.g., wherein the third criterion is indicative of the current change between the first and second currents).

An electrode in a surgical environment with the vapor pocket 114 can draw energy of a first voltage, while the same electrode in the surgical environment with the vapor pocket 114 can draw energy of a second voltage. The second voltage is greater than the first voltage. Thus, detecting the vapor pocket 114 is present can include determining the voltage of power from the energy supply 104 has changed by a fourth criterion (e.g., wherein the fourth criterion is indicative of the voltage change between the first and second voltages).

The control circuitry 550, in response to detecting the vapor pocket 114 is present can reduce an amount of power supplied to the electrodes 106 by the energy supply 104. The amount of power provided in response to detecting the vapor pocket 114 is present can be sufficient to retain the vapor pocket 114, but less than an amount of energy required to generate the vapor pocket 114.

The control circuitry 550 can, after detecting the vapor pocket 114, can close a switch electrically connected between the secondary electrode of the electrodes 106 and the energy supply 104. Closing the switch can complete an energy path between the energy supply 104 and the secondary electrode. The control circuitry 550 can thus cause energy to be supplied to the secondary electrode. Activating the secondary electrode by closing the switch and completing an energy path to the secondary electrode can increase an amount of the surgery target 108 affected per unit time.

The control circuitry 550 can, after detecting the vapor pocket 114 is not present, open the electrical path between the energy supply 104 and the secondary electrode. The control circuitry 550 can, for example, detect that the resistance to power of the energy supply 104 has decreased by the first criterion, the phase angle of power from the energy supply 104 has changed by the second criterion, the current of power from the energy supply has increased by the third criterion, the voltage of power from the energy supply 104 has decreased by the fourth criterion, or a combination thereof. Any one or more of these can indicate that the vapor pocket 114 has dissipated.

The control circuitry 550 can, after detecting the vapor pocket 114 is present, activate or increase a fluid rate of fluid from the fluid supply/return 120. Activating the fluid supply/return 120 can cause fluid 110 to be provided through the outlet port 116, fluid 110 to be removed from the cavity through the suction port 118, or a combination thereof. The control circuitry 550 can, after detecting the vapor pocket 114 is not present, deactivate or reduce a fluid rate of fluid the fluid supply/return 120. Deactivating the fluid supply/return 120 can stop fluid from flowing to the outlet port 116, being returned to the fluid supply/return 120 through the suction port 118, or a combination thereof.

In some instances, the fluid supply/return 120 operation can be independent of existence of the vapor pocket 114. That is, the fluid supply/return 120 can provide or remove fluid 110 based on some other, non-vapor pocket, criteria. For example, the control circuitry 550 can activate or deactivate the fluid supply/return 120 responsive to providing energy to the primary electrode from the energy supply 104, the control circuitry can activate or deactivate the fluid supply/return 120 responsive to providing energy to the primary and secondary electrodes, or a combination thereof.

The control circuitry 550 can include an impedance sensor, such as can use the electrosurgical signal or a separate electrical test signal to deliver a specified current or voltage to the tissue and measure a responsive voltage or current indicative of tissue impedance, such as when the series impedance of the leads or electrodes are subtracted. A three-point or four-point probe or similar impedance sensing electrode arrangement can be used, such as to permit sensing of the response variable via a high input impedance sensing interface amplifier separate from the effects of the larger test or electrosurgical signal passing through the impedance of the leads connected to electrodes used for delivering such signals. For example, such a three-point or four-point probe can use bipolar electrodes for delivering the test or electrosurgical signal and can include one or more additional electrodes for sensing the response variable into the high input impedance sensing interface amplifier. Thus, the impedance sensor can include using one or more of the electrodes 106, additional, or separate impedance sensing electrodes, or other impedance sensors can be provided. In some cases, an impedance value can be measured or sensed by monitoring the electrode itself without the use of an additional sensor.

Impedance information can also include phase angle information, such as can describe the phase relationship between current and voltage in an alternating current (AC) circuit, such as in a high frequency AC electrosurgery application. The phase angle can describe the phase difference between the voltage applied to the tissue impedance and the current driven through it. Because tissue impedance can include reactive components such as capacitance or inductance, the resulting current will either lag behind the applied voltage (e.g., phase shift due to inductive components) or lead the applied voltage (e.g., phase shift due to capacitive components). Phase angle can be determined, for example, between current and voltage at a given time by comparing the times corresponding to detected edges or other reference or threshold values of current and voltage.

Phase angle signal-processing circuitry can accomplish this comparison such as applying a technique such as a Discrete Fourier Transform (DFT). For example, samples of a signal being analyzed can be correlated point-by-point, such as with each of both a sine function and a cosine function. Arbitrarily, the cosine part can be called real, and the sine part can be called imaginary. If the signal being analyzed has no phase shift, the result of the DFT is 100% real. If the signal being analyzed has a 90-degree phase shift, the result of the DFT is 100% imaginary. If the result of the DFT has both a real and imaginary component, the phase angle can be calculated as the arctangent of a ratio of the imaginary and real values.

One or more electrical properties of the target tissue, such as conductivity, resistivity, impedance, or phase angle, can be sensed throughout electrosurgery, or during one or more "sensing pulses," such as can be sent out intermittently during electrosurgery.

Figures 6, 7:
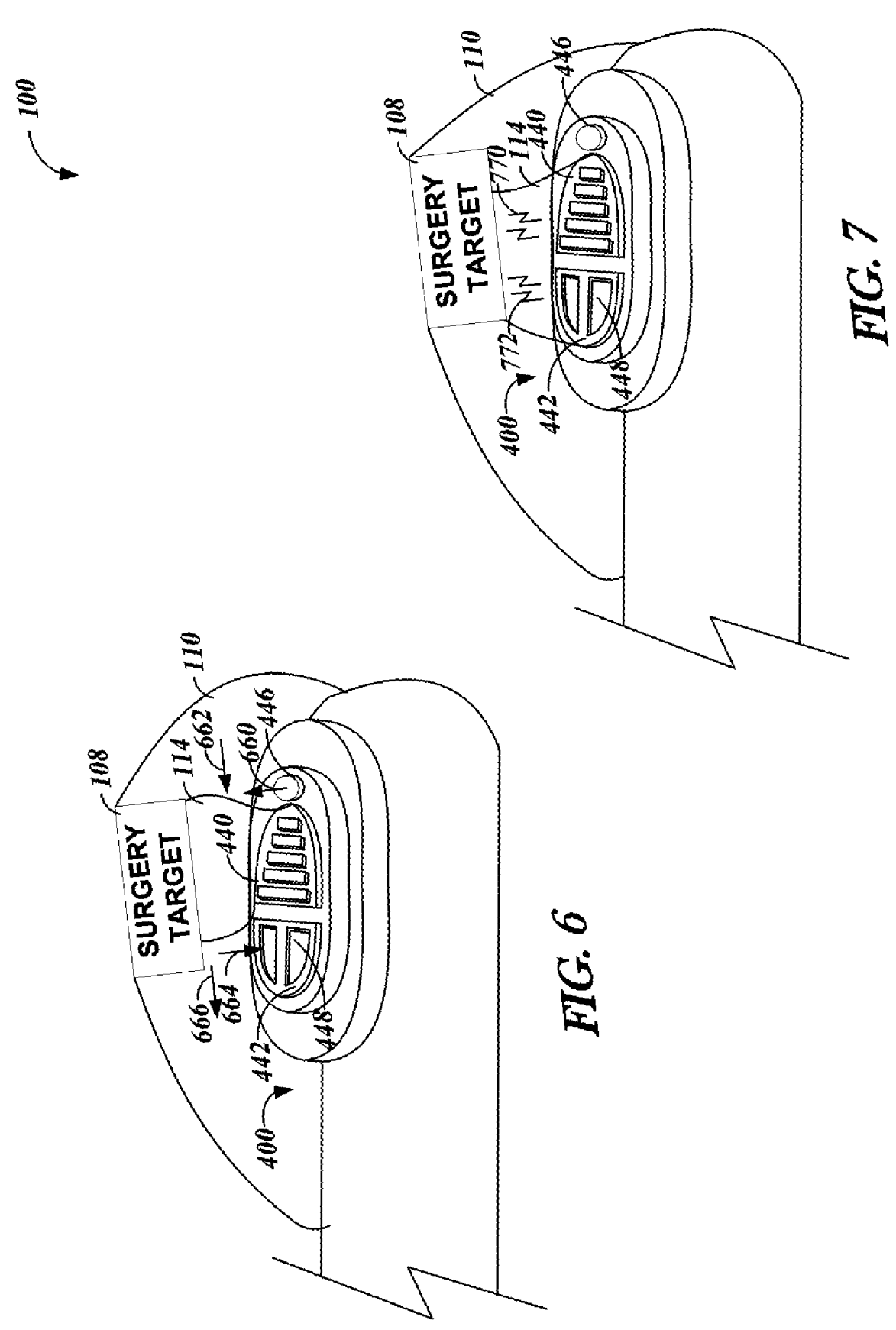
FIG. 6 illustrates, by way of example, a diagram of an embodiment of a system that includes the electrosurgical device after generation of the vapor pocket.
FIG. 7 illustrates, by way of example, a diagram of the system of FIG. 6 after the vapor pocket is situated between both the primary and secondary electrodes and the surgery target.

FIG. 6 illustrates, by way of example, a diagram of an embodiment of a system that includes the electrosurgical device 400 after generation of the vapor pocket 114. The energy supply 104 can provide energy to the electrode 440 that causes the electrode 440 to vaporize a portion of the fluid 110 and create the vapor pocket 114. The electrode 440 can then vaporize a portion of the surgery target 108 accessible through the vapor pocket 114.

As previously discussed, the control circuitry 550 can detect presence of the vapor pocket 114 in a variety of ways. The control circuitry 550 can perform a variety of actions responsive to detecting the vapor pocket 114. One such action is causing the fluid supply/return 120 to provide the fluid 110 to the output port 446. The fluid 110 can exit the outlet port 446 in a direction indicated by arrow 660. The fluid 110 travelling in the direction indicated by arrow 660 can push the vapor pocket 114 towards the secondary electrode (e.g., the electrode 442 in the example of FIG. 6) in the direction indicated by arrow 662.

Another such action is causing the fluid supply/return 120 to remove some of the fluid 110 from the cavity. The removal of the fluid 110 can cause some of the fluid 110 to travel in a direction indicated by arrow 664. Such travel of the fluid 110 can pull the vapor pocket 114 towards the secondary electrode (e.g., the electrode 442 in the example of FIG. 6) in the direction indicated by arrow 666.

Such pulling or pushing of the vapor pocket 114 can help position the vapor pocket 114 over both the primary electrode (e.g., the electrode 440 in the example of FIG. 6) and the secondary electrode. With the vapor pocket 114 between both the primary and second electrodes and the surgery target 108, both the primary and secondary electrodes can vaporize the surgery target concurrently. This increases an amount of the surgery target 108 that can be affected by the electrosurgical device 400 per unit time as compared to a device that includes the primary electrode as the only active electrode.

FIG. 7 illustrates, by way of example, a diagram of the system of FIG. 6 after the vapor pocket 114 is situated between both the primary and secondary electrodes and the surgery target 108. The electrodes 440, 442 can concurrently vaporize the target 108 (indicated by lightning bolts 770, 772) in such a configuration.

Figure 8:
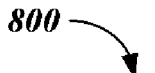
FIG. 8 illustrates, by way of example, a diagram of an embodiment of a method 800 for operating an electrosurgical system, such as one of the electrosurgical systems discussed herein.
Figure 8:
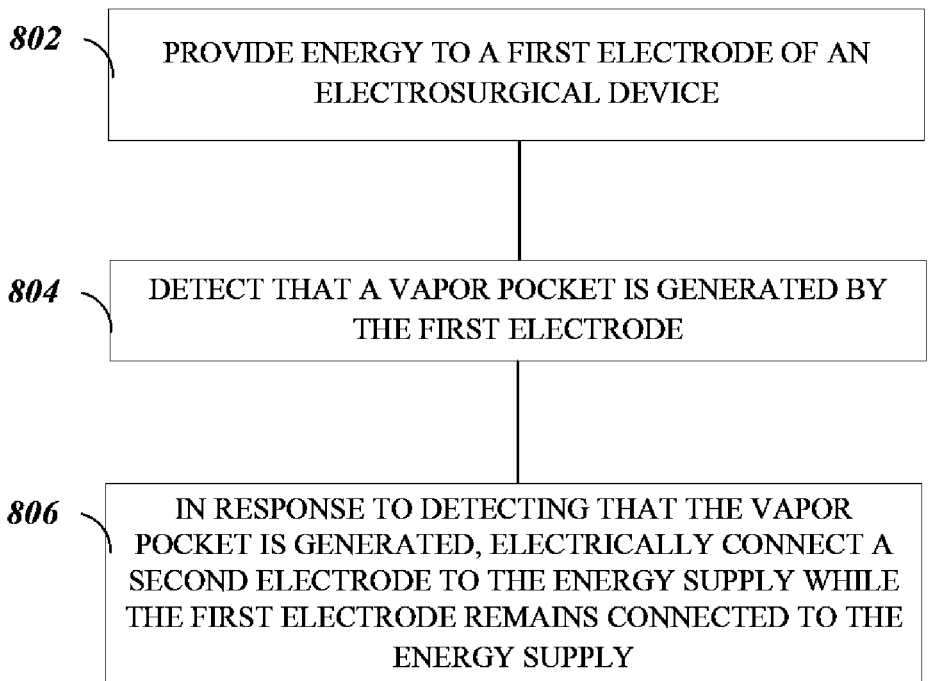

FIG. 8 illustrates, by way of example, a diagram of an embodiment of a method 800 for operating an electrosurgical system, such as one of the electrosurgical systems discussed herein. The method 800 can include providing, by an energy supply 104, energy to a first electrode 106, 440, 442 of an electrosurgical device 102, 200, 400, at operation 802; detecting, by control circuitry 550, that a vapor pocket 114 is generated by the first electrode 106, 440, 442, at operation 804; and in response to detecting that the vapor pocket is generated, electrically connecting, by the control circuitry 550, a second electrode 106, 442, 440 to the energy supply 104 while the first electrode 106, 440, 442 remains electrically connected to the energy supply 104, at operation 806.

The method 800 can further include, wherein detecting that the vapor pocket 114 is generated includes determining that a resistance to the energy has increased by a first criterion. The method 800 can further include, wherein detecting that the vapor pocket 114 is generated includes determining that a phase angle of the energy has changed by a second criterion. The method 800 can further include, wherein detecting that the vapor pocket is generated includes determining that a current of the energy has decreased by a third criterion. The method 800 can further include, wherein detecting the vapor pocket is generated includes determining that a voltage of the energy has increased by a fourth criterion. Any of the first, second, third, and fourth criterion can be determined through testing of the electrosurgical device 102, 200, 400. The resistance, phase angle, current, voltage, or the other parameter can be determined in empirical conditions. The determined parameter can then inform the criterion that are used to determine whether the vapor pocket 114 exists or not.

The method 800 can further include, wherein the control circuitry 550 is further configured to reduce a magnitude of the energy in response to detecting that the vapor pocket 114 is generated. The method 800 can further include activating, by the control circuitry 550, a suction port 118 of the electrosurgical device in response to detecting that the vapor pocket 114 is generated. The method 800 can further include deactivating, by the control circuitry 550, the suction port 118 in response to detecting that the vapor pocket 114 has dissipated.

The method 800 can further include causing, by the control circuitry 550, fluid to flow to a fluid outlet port 116 of the electrosurgical device in response to detecting that the vapor pocket 114 is generated. The method 800 can further include restricting, by the control circuitry 550, fluid flow in the fluid outlet port 116 in response to detecting that the vapor pocket 114 has dissipated.

Figure 9:
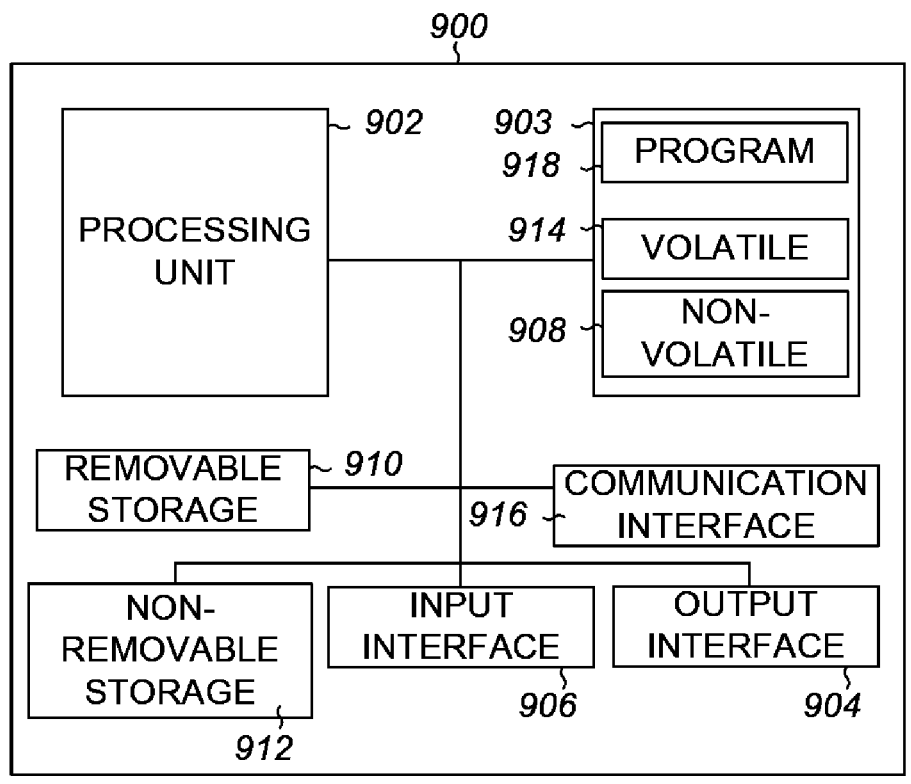
FIG. 9 illustrates, by way of example, a block diagram of an embodiment of a machine (e.g., a computer system) to implement one or more embodiments.

FIG. 9 illustrates, by way of example, a block diagram of an embodiment of a machine 900 (e.g., a computer system) to implement one or more embodiments. The control circuitry 550 can include or be implemented using one or more components of the machine 900. One example machine 900 (in the form of a computer), may include a processing unit 902, memory 903, removable storage 910, and non-removable storage 912. Although the example computing device is illustrated and described as machine 900, the computing device may be in different forms in different embodiments. For example, the computing device may instead be a smartphone, a tablet, smartwatch, or other computing device including the same or similar elements as illustrated and described regarding FIG. 9. Devices such as smartphones, tablets, and smartwatches are generally collectively referred to as mobile devices. Further, although the various data storage elements are illustrated as part of the machine 900, the storage may also or alternatively include cloud-based storage accessible via a network, such as the Internet.

Memory 903 may include volatile memory 914 and non-volatile memory 908. The machine 900 may include—or have access to a computing environment that includes—a variety of computer-readable media, such as volatile memory 914 and non-volatile memory 908, removable storage 910 and non-removable storage 912. Computer storage includes random access memory (RAM), read only memory (ROM), erasable programmable read-only memory (EPROM) & electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage or other magnetic storage devices capable of storing computer-readable instructions for execution to perform functions described herein.

The machine 900 may include or have access to a computing environment that includes input 906, output 904, and a communication connection 916. Output 904 may include a display device, such as a touchscreen, that also may serve as an input device. The input 906 may include one or more of a touchscreen, touchpad, mouse, keyboard, camera, one or more device-specific buttons, one or more sensors integrated within or coupled via wired or wireless data connections to the machine 900, and other input devices. The computer may operate in a networked environment using a communication connection to connect to one or more remote computers, such as database servers, including cloud based servers and storage. The remote computer may include a personal computer (PC), server, router, network PC, a peer device or other common network node, or the like. The communication connection may include a Local Area Network (LAN), a Wide Area Network (WAN), cellular, Institute of Electrical and Electronics Engineers (IEEE) 802.11 (Wi-Fi), Bluetooth, or other networks.

Computer-readable instructions stored on a computer-readable storage device are executable by the processing unit 902 of the machine 900. A hard drive, CD-ROM, and RAM are some examples of articles including a non-transitory computer-readable medium such as a storage device. For example, a computer program 918 may be used to cause processing unit 902 to perform one or more methods or algorithms described herein.

The method steps disclosed herein can be performed in any order except as specified otherwise. Moreover, one or more of the method steps can be combined with other steps; can be omitted or eliminated; can be repeated; and/or can separated into individual or additional steps.

The explanations and illustrations presented herein are intended to acquaint others skilled in the art with the invention, its principles, and its practical application. The above description is intended to be illustrative and not restrictive.

Those skilled in the art may adapt and apply the teachings in its numerous forms, as may be best suited to the requirements of a particular use.

Accordingly, the embodiments of the present teachings as set forth are not intended as being exhaustive or limiting of the teachings. Further, components of the specific embodiments can be combined with components of other embodiments of the teachings. The scope of the teachings should, therefore, be determined not with reference to this description, but should instead be determined with reference to the appended claims, along with the full scope of equivalents to which such claims are entitled. The omission in the following claims of any aspect of subject matter that is disclosed herein is not a disclaimer of such subject matter, nor should it be regarded that the inventors did not consider such subject matter to be part of the disclosed inventive subject matter.

Plural elements or steps can be provided by a single integrated element or step. Alternatively, a single element or step might be divided into separate plural elements or steps. The disclosure of "a" or "one" to describe an element or step is not intended to foreclose additional elements or steps. While the terms first, second, third, etc., may be used herein to describe various elements, components, regions, layers and/or sections, these elements, components, regions, layers and/or sections should not be limited by these terms. These terms may be used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. An electrosurgical device comprising:
a return electrode exposed on an outer surface of a dielectric;
a first electrode exposed on the outer surface of the dielectric;
a second electrode exposed on the outer surface of the dielectric; and
a suction port exposed on the outer surface of the dielectric and situated to (i) draw a vapor pocket generated by the first electrode to the second electrode and (ii) retain the vapor pocket at the suction port.

2. The device of claim 1, further comprising a dielectric covering a portion of the first electrode.

3. The device of claim 1, further comprising a fluid outlet port situated to direct, by fluid flowing therethrough towards a target, the vapor pocket generated by the first electrode to the second electrode.

4. The device of claim 1, further comprising a switch component configured to concurrently connect both the first electrode and the second electrode to an energy supply.

5. The device of claim 1, wherein the second electrode at least partially surrounds the suction port.

6. The device of claim 5, wherein the suction port is completely surrounded by the second electrode.

7. An electrosurgical system comprising:
an electrosurgical device comprising:
a dielectric;
a return electrode exposed on an outer surface of the dielectric;
a first electrode exposed on the outer surface of the dielectric;
a second electrode exposed on the outer surface of the dielectric;
an energy supply configured to provide energy to the electrosurgical device;
a fluid outlet port configured to provide fluid to a target and situated to (i) push a vapor pocket generated by the first electrode to the second electrode and (ii) retain the vapor pocket at the second electrode; and
control circuitry configured to, in response to detecting a vapor pocket at the first electrode, electrically connect the second electrode to the energy supply concurrently with the first electrode and cause fluid to flow to the fluid outlet port in response to detecting the vapor pocket.

8. The system of claim 7, wherein detecting the vapor pocket includes determining whether a resistance to energy of the energy supply has increased by a first criterion.

9. The system of claim 7, wherein detecting the vapor pocket includes determining whether a phase angle of energy from the energy supply has changed by a second criterion.

10. The system of claim 7, wherein detecting the vapor pocket includes determining whether a current of energy from the energy supply has decreased by a third criterion.

11. The system of claim 7, wherein detecting the vapor pocket is generated includes determining whether a voltage of energy from the energy supply has increased by a fourth criterion.

12. The system of claim 7, wherein the control circuitry is further configured to reduce a magnitude of the energy provided to the device in response to detecting the vapor pocket.

13. The system of claim 7, wherein:
the electrosurgical device further includes a suction port; and
the control circuitry is configured to activate the suction port in response to detecting the vapor pocket.

14. The system of claim 13, wherein the control circuitry is configured to deactivate the suction port in response to detecting that the vapor pocket has dissipated.

15. The system of claim 7, wherein the control circuitry is configured to restrict fluid flow in the fluid outlet port in response to detecting that the vapor pocket has dissipated.

16. A method of operating an electrosurgical system, the method comprising:
providing, by an energy supply, energy to a first electrode of an electrosurgical device;
detecting, by control circuitry, that a vapor pocket is generated by the first electrode by determining that a phase angle of the energy has changed by a first criterion;
in response to detecting that the vapor pocket is generated, electrically connecting, by the control circuitry, a second electrode to the energy supply while the first electrode remains electrically connected to the energy supply; and activating a suction port to (i) draw a vapor pocket generated by the first electrode to the second electrode and (ii) retain the vapor pocket at the second electrode.

17. The method of claim 16, wherein detecting that the vapor pocket is generated includes determining that a resistance to the energy has increased by a second criterion.

18. The method of claim 16, wherein detecting that the vapor pocket is generated includes determining that a current of the energy has decreased by a third criterion.

19. The method of claim 16, wherein detecting the vapor pocket is generated includes determining that a voltage of the energy has increased by a fourth criterion.

20. The method of claim 16, wherein the control circuitry is further configured to reduce a magnitude of the energy in response to detecting that the vapor pocket is generated.

21. The method of claim 16, further comprising activating, by the control circuitry, a suction port of the electrosurgical device in response to detecting that the vapor pocket is generated.

22. The method of claim 21, further comprising, deactivating by the control circuitry, the suction port in response to detecting that the vapor pocket has dissipated.

23. The method of claim 16, further comprising causing, by the control circuitry, fluid to flow to a fluid outlet port of the electrosurgical device in response to detecting that the vapor pocket is generated.

24. The method of claim 23, further comprising restricting, by the control circuitry, fluid flow in the fluid outlet port in response to detecting that the vapor pocket has dissipated.

\* \* \* \* \*